US00PP30981P2

(12) United States Plant Patent
Konings

(10) Patent No.: US PP30,981 P2
(45) Date of Patent: Oct. 29, 2019

(54) STRAWBERRY PLANT NAMED 'P061105'

(50) Latin Name: ***Fragaria* x *ananassa***
Varietal Denomination: P061105

(71) Applicant: Hubertus Antonius Maria Konings, America (NL)

(72) Inventor: Hubertus Antonius Maria Konings, America (NL)

(73) Assignee: Vissers America B.V., America (NL)

( * ) Notice: Subject to any disclaimer, the term of this patent is extended or adjusted under 35 U.S.C. 154(b) by 0 days.

(21) Appl. No.: 15/932,823

(22) Filed: Apr. 30, 2018

(51) Int. Cl.
*A01H 5/08* (2018.01)
*A01H 6/74* (2018.01)

(52) U.S. Cl.
USPC ..... Plt./208
CPC ..... *A01H 6/74* (2018.05); *A01H 5/08* (2013.01)

(58) Field of Classification Search
USPC ..... Plt./208, 209
CPC ..... A01H 5/0893
See application file for complete search history.

(56) References Cited

PUBLICATIONS

GTITM UPOVROM Citation for 'P061105' as per QZ PBR 20151654; Oct. 15, 2015; 1 page.*

* cited by examiner

*Primary Examiner* — Kent L Bell
(74) *Attorney, Agent, or Firm* — C. A. Whealy

(57) ABSTRACT

A new and distinct cultivar of Strawberry plant named 'P061105', characterized by its upright plant habit; moderately vigorous to vigorous growth habit; uniform fruit ripening; large conical fruits that are glossy and orange red in color with seeds positioned slightly below the surface; pleasant fruit aroma and taste; good fruit postharvest longevity; long flowering and fruit harvesting period; and low susceptibility to *Podosphaera aphanis* (powdery mildew) and *Phytophthora cactorum*.

2 Drawing Sheets

Botanical designation: *Fragaria* x *ananassa*.
Cultivar denomination: 'P061105'.

BACKGROUND OF THE INVENTION

The present Invention relates to a new and distinct cultivar of Strawberry plant, botanically known as *Fragaria* x *ananassa* and hereinafter referred to by the name 'P061105'.

The new Strawberry plant is a product of a planned breeding program conducted by the Inventor in America, The Netherlands. The objective of the breeding program was to develop new Strawberry plants with good fruit quality, ease of harvesting, good postharvest longevity and resistance to pathogens.

The new Strawberry plant originated from a cross-pollination in 2009 in America, The Netherlands of two unnamed proprietary selections of *Fragaria* x *ananassa*, not patented. The new Strawberry plant was discovered and selected by the Inventor as a single plant from within the progeny of the stated cross-pollination in a controlled environment in America, The Netherlands in 2010.

Asexual reproduction of the new Strawberry plant by vegetative cuttings in a controlled environment at America, The Netherlands since 2010 has shown that the unique features of this new Strawberry plant are stable and reproduced true to type in successive generations of asexual reproduction.

SUMMARY OF THE INVENTION

Plants of the new Strawberry have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'P061105'. These characteristics in combination distinguish 'P061105' as a new and distinct Strawberry plant:

1. Upright plant habit.
2. Moderately vigorous to vigorous growth habit.
3. Uniform fruit ripening.
4. Large conical fruits that are glossy and orange red in color with seeds positioned slightly below the surface.
5. Pleasant fruit aroma and taste.
6. Good fruit postharvest longevity.
7. Long flowering and fruit harvesting period.
8. Low susceptibility to *Podosphaera aphanis* (powdery mildew) and *Phytophthora cactorum*.

Plants of the new Strawberry differ primarily from plants of the female parent selection in the following characteristics:

1. Plants of the new Strawberry produce fewer fruits per truss, but larger fruits than plants of the female parent selection.
2. Fruits of plants of the new Strawberry are firmer than fruits of plants of the female parent selection.
3. Fruits of plants of the new Strawberry are more flavorful than fruits of plants of the female parent selection.

Plants of the new Strawberry differ primarily from plants of the male parent selection in the following characteristics:

1. Plants of the new Strawberry produce larger fruits than plants of the male parent selection.
2. Fruits of plants of the new Strawberry are firmer than fruits of plants of the male parent selection.
3. Plants of the new Strawberry have low susceptibility to *Podosphaera aphanis* whereas plants of the male parent selection are susceptible to *Podosphaera aphanis*.

Plants of the new Strawberry can be compared to plants of *Fragaria* x *ananassa* 'Mailing Centenary', not patented. In side-by-side comparisons, plants of the new Strawberry differ primarily from plants of 'Mailing Centenary' in the following characteristics:

1. Fruits of plants of the new Strawberry ripen later than fruits of plants of 'Mailing Centenary'.
2. Fruits of plants of the new Strawberry are glossier than fruits of plants of 'Mailing Centenary'.
3. Fruits of plants of the new Strawberry have seeds positioned slightly below the surface whereas fruits of plants of 'Mailing Centenary' have seeds positioned at the surface level.

Plants of the new Strawberry can be compared to plants of *Fragaria* x *ananassa* 'Florence', not patented. In side-by-side comparisons plants of the new Strawberry differ primarily from plants of 'Florence' in the following characteristics:

1. Fruits of plants of the new Strawberry ripen later than fruits of plants of 'Florence'.
2. Fruits of plants of the new Strawberry are orange red in color whereas fruits of plants of 'Florence' are darker red in color.
3. Fruits of plants of the new Strawberry have seeds positioned slightly below the surface whereas fruits of plants of 'Florence' have seeds positioned at the surface level.

Plants of the new Strawberry can be compared to plants of *Fragaria* x *ananassa* 'Cristina', disclosed in U.S. Plant Pat. No. 24,511. In side-by-side comparisons plants of the new Strawberry differ primarily from plants of 'Cristina' in the following characteristics:

1. Plants of the new Strawberry are more upright and more vigorous than plants of 'Cristina'.
2. Plants of the new Strawberry produce more fruits than plants of 'Cristina'.
3. Fruits of plants of the new Strawberry are darker orange red in color than fruits of plants of 'Cristina'.
4. Fruits of plants of the new Strawberry are glossier than fruits of plants of 'Cristina'.
5. Fruits of plants of the new Strawberry have seeds positioned slightly below the surface whereas fruits of plants of 'Cristina' have seeds positioned at the surface level.
6. Plants of the new Strawberry have low susceptibility to *Phytophthora cactorum* and *Podosphaera aphanis* whereas plants of 'Cristina' are susceptible to most pathogens common to Strawberry plants.

BRIEF DESCRIPTION OF THE PHOTOGRAPHS

The accompanying colored photographs illustrate the overall appearance of the new Strawberry plant showing the colors as true as it is reasonably possible to obtain in colored reproductions of this type. Colors in the photographs may differ slightly from the color values cited in the detailed botanical description which accurately describe the colors of the new Strawberry plant.

The photograph on the first sheet is a side perspective view of typical flowering plants of 'P061105' grown in trays.

The photograph on the second sheet is a close-up view of typical developing and developed fruits of 'P061105'.

DETAILED BOTANICAL DESCRIPTION

The aforementioned photographs, following observations and measurements describe plants grown in 200-cc trays during the spring, summer and autumn in a polyethylene-covered greenhouse in America, The Netherlands and under cultural practices typical of commercial Strawberry production. During the production of the plants, day temperatures ranged from 5° C. to 25° C. and night temperatures ranged from 1° C. to 12° C. Plants were four to five months from planting when the photographs and description were taken. In the following description, color references are made to The Royal Horticultural Society Colour Chart, 2001 Edition, except where general terms of ordinary dictionary significance are used.

Botanical classification: *Fragaria* x *ananassa* 'P061105'.

Parentage:

*Female, or seed, parent*.—Unnamed proprietary selection of *Fragaria* x *ananassa*, not patented.

*Male, or pollen, parent*.—Unnamed proprietary selection of *Fragaria* x *ananassa*, not patented.

Propagation:

*Type*.—By vegetative cuttings.

*Time to initiate roots, summer*.—About one to four days at soil temperatures about 15° C.

*Time to produce a rooted young plant, summer*.—About four weeks at soil temperatures ranging from 18° to 20° C.

*Root description*.—Medium in thickness, fibrous; typically cream to white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Perennial; upright plant habit; leaves basal; moderately vigorous to vigorous growth habit; moderate growth rate; fairly densely foliated and somewhat open canopy.

*Plant height*.—About 20 cm to 40 cm.

*Plant diameter*.—About 30 cm to 50 cm.

*Stolon texture*.—Moderately pubescent.

*Stolon color*.—Close to 144B.

Leaf description:

*Arrangement and appearance*.—Basal rosette; compound with typically three or four leaflets per leaf; leaves non-variegated.

*Leaflet length*.—About 11 cm to 12 cm.

*Leaflet width*.—About 11 cm to 12 cm.

*Leaflet shape*.—Broadly ovate.

*Leaflet apex*.—Obtuse, emarginate.

*Leaflet base*.—Obtuse to rounded.

*Leaflet margin*.—Crenate.

*Leaflet texture and luster, upper surface*.—Smooth, glabrous; moderately glossy.

*Leaflet texture and luster, lower surface*.—Pubescent, rough; matte.

*Leaflet venation*.—Pinnate.

*Leaflet color*.—Developing leaflets, upper surface: Close to 137A. Developing leaflets, lower surface: Close to 138A. Fully expanded leaflets, upper surface: Close to between 137A and 139A; venation, close to 144C. Fully expanded leaflets, lower surface: Close to 138A; venation, close to 144C.

*Petioles*.—Length: About 15 cm to 20 cm. Diameter: About 2.5 mm to 6 mm. Texture, upper and lower surfaces: Pubescent. Color, upper and lower surfaces: Close to 145A.

Flower description:

*Flower form and flowering habit*.—Rotate flowers arranged singly at lateral apices; flowers held at or slightly below the foliar plane; about five to seven flowers per truss and more than 80 developing per plant; flowers are self-fertile.

*Fragrance*.—None detected.

*Natural flowering season*.—Long flowering period; plants flower in April and May in The Netherlands.

*Flower diameter*.—About 2 cm to 3 cm.

*Flower depth* (*height*).—About 8 mm to 12 mm.

*Petals*.—Arrangement: Single whorl of seven or eight petals; petals slightly imbricate. Length: About 8 mm to 12 mm. Width: About 8 mm to 10 mm. Shape: Round to broadly ovate. Apex: Rounded. Base: Attenuate. Margin: Entire. Texture, upper and lower surfaces: Smooth, glabrous; satiny. Color: When opening and fully opened, upper surface: Close to 155D. When opening and fully opened, lower surface: Close to 155D.

*Sepals*.—Arrangement and calyx description: Two whorls of six to ten sepals per whorl; calyx, star-shaped; calyx adherence is weak to moderate; sepals are orientated towards the fruit. Calyx length: About 1 cm to 1.5 cm. Calyx diameter: About 1 cm to 2 cm. Length: About 8 mm to 14 mm. Width: About 5 mm to 10 mm. Shape: Lanceolate to ovate. Apex: Acute. Base: Fused. Margin: Entire. Texture, upper and lower surfaces: Smooth, glabrous. Color, upper and lower surfaces: Close to 137A.

*Peduncles*.—Length: About 5 cm to 10 cm. Diameter: About 1 mm to 2 mm. Strength: Strong. Texture: Pubescent. Color: Close to 144B.

*Pedicels*.—Length: About 3 cm to 8 cm. Diameter: About 1 mm to 3 mm. Strength: Strong. Aspect: About 90° from the peduncle axis. Texture: Smooth, glabrous. Color: Close to 144B.

*Reproductive organs*.—Stamens: Quantity per flower: About 25. Anther length: About 3 mm. Anther shape: Lanceolate to elliptic. Anther color: Close to 8A. Pollen amount: Abundant. Pollen color: Close to 6A. Pistils: Quantity per flower: More than 250. Pistil length: About 1 mm to 2 mm. Stigma shape: Rounded. Stigma color: Close to 5A. Fruits: Quantity per truss: About five to seven. Natural fruiting season: Plants produce fruit from early June to mid-July in The Netherlands; fruits fully ripen in about four weeks. Postharvest longevity: About seven to ten days at 4° C. Length: About 3 cm to 3.5 cm. Diameter: About 2 cm to 4 cm. Shape: Conical. Fruit weight per fruit, first quality: About 22 g to 28 g. Fruit weight per plant, first quality: About 370 g. Firmness: Firm. Fragrance, taste: Pleasant; good balance between sweetness and acidity. Luster: Uniformly glossy; very glossy. Surface unevenness: Smooth. Color, surface: Close to 34A. Color, flesh: Close to 33C to 33D. Seed density: Medium. Achene position: Positioned slightly below the surface, slightly indented. Achene color: Close to 32A.

Disease and pest resistance: Plants of the new Strawberry have been observed to have low susceptibility to *Podosphaera aphanis* (formerly known as *Sphaerotheca macularis*) and *Phytophthora cactorum*. Plants of the new Strawberry have not been observed to be resistant to pests and other pathogens common to Strawberry plants.

It is claimed:

1. A new and distinct Strawberry plant named 'P061105' as illustrated and described.

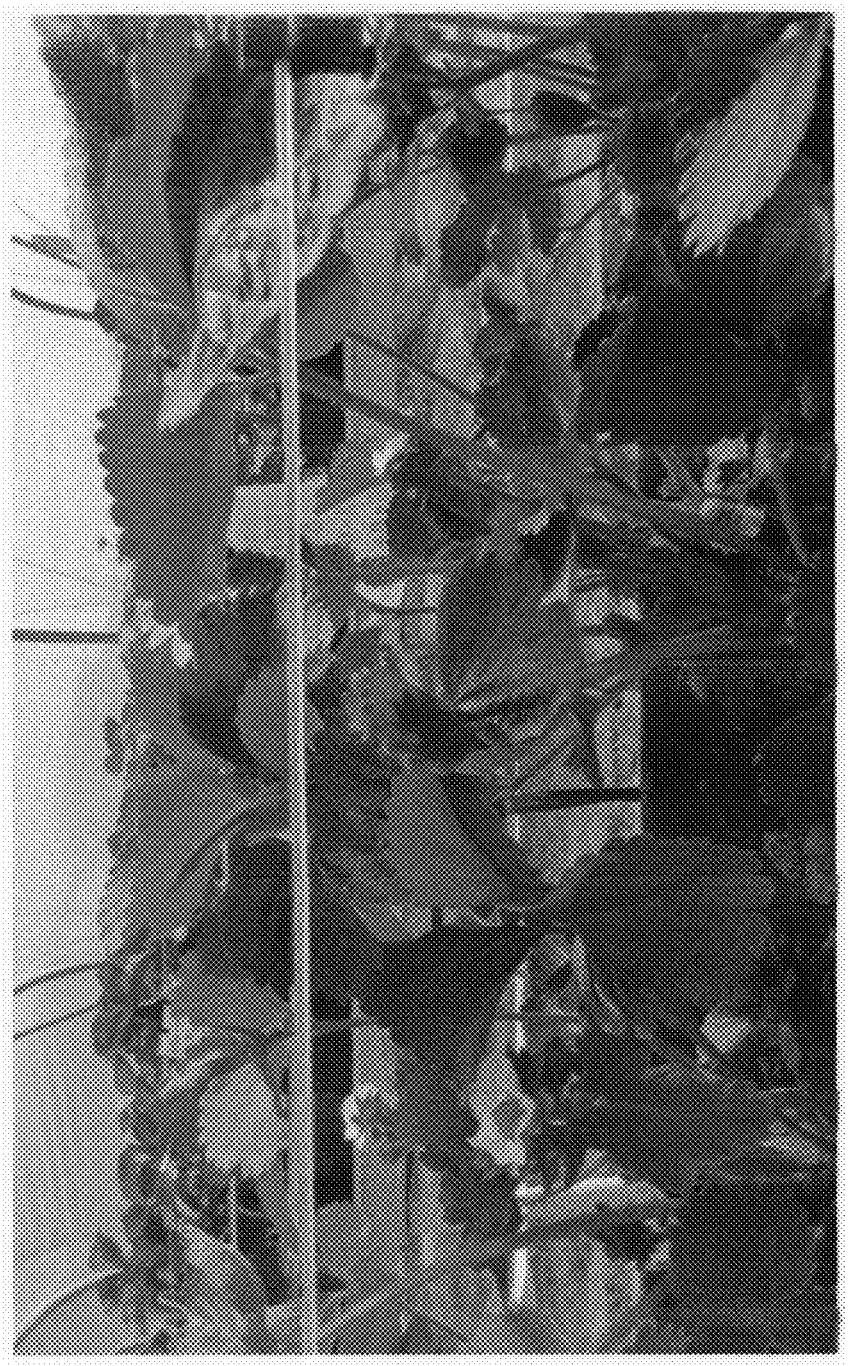

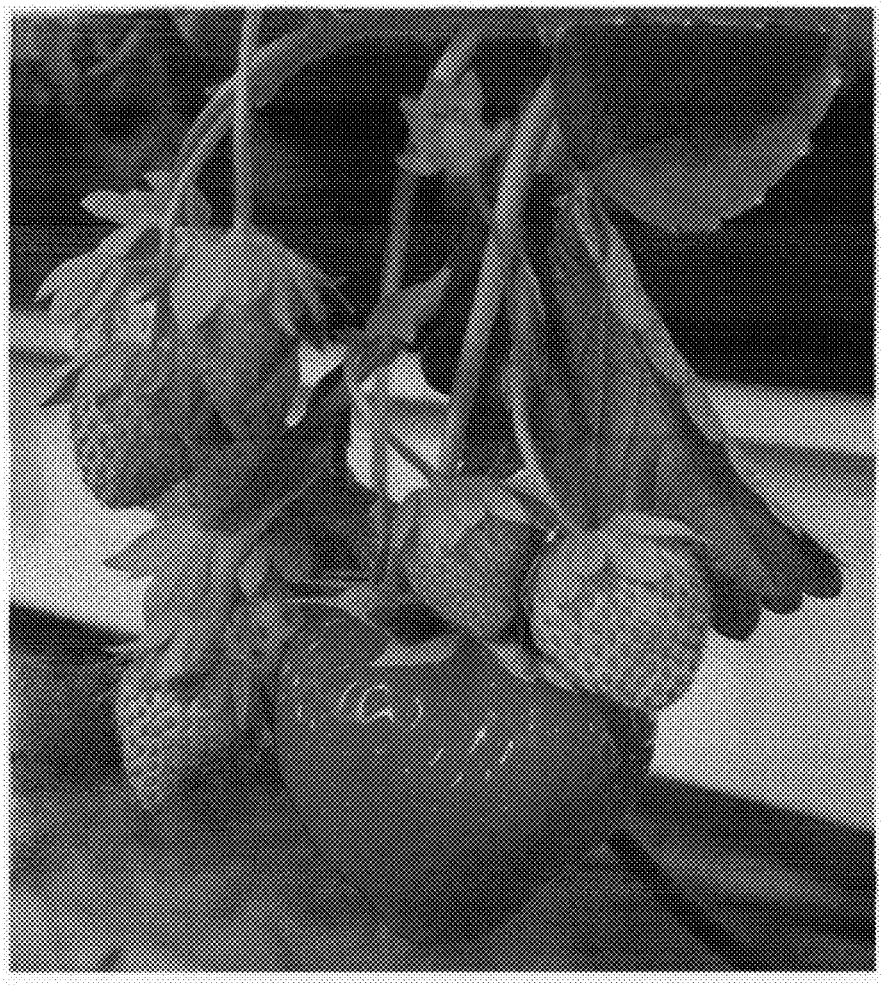

* * * * *